US008346632B2

(12) United States Patent
Saghbini

(10) Patent No.: US 8,346,632 B2
(45) Date of Patent: Jan. 1, 2013

(54) RECALL SYSTEM AND METHOD FOR RFID MEDICAL ITEM TRACKING SYSTEM

(75) Inventor: Jean-Claude Saghbini, Cambridge, MA (US)

(73) Assignee: WaveMark, Inc., Littleton, MA (US)

( * ) Notice: Subject to any disclaimer, the term of this patent is extended or adjusted under 35 U.S.C. 154(b) by 513 days.

(21) Appl. No.: 12/203,171

(22) Filed: Sep. 3, 2008

(65) Prior Publication Data

US 2010/0036755 A1  Feb. 11, 2010

Related U.S. Application Data

(60) Provisional application No. 61/086,998, filed on Aug. 7, 2008.

(51) Int. Cl.
*G06Q 10/00* (2012.01)
(52) U.S. Cl. ............................................. 705/28; 705/2
(58) Field of Classification Search ...................... 705/28
See application file for complete search history.

(56) References Cited

U.S. PATENT DOCUMENTS

| 7,685,026 | B1* | 3/2010 | McGrady et al. | ............... | 705/28 |
| 2008/0011849 | A1* | 1/2008 | Silverbrook et al. | ......... | 235/439 |
| 2008/0024310 | A1* | 1/2008 | Baker et al. | ................ | 340/572.8 |
| 2008/0029532 | A1 | 2/2008 | Handfield et al. | | |
| 2008/0059228 | A1 | 3/2008 | Bossi et al. | | |

OTHER PUBLICATIONS

"Medical Equipment Tracking in a Health Care System", Dr. James S. Noble, Dec. 2006.*

* cited by examiner

*Primary Examiner* — Garcia Ade
(74) *Attorney, Agent, or Firm* — Houston & Associates, LLP

(57) ABSTRACT

A medical item recall system for medical items at one or more medical facilities at which the medical items are consumed and/or distributed to patients provides each of the medical items has stand-off readable tags, such as RFID tags. The system comprises medical facilities storage devices at the one or more medical facilities containing medical items, the medical items being identified via the stand-off readable tags and associated with individual medical facilities storage devices. The system further comprises an inventory management system that receives recall information for the medical items, receives content information concerning the medical items contained in each of the medical facilities storage devices, and issues reports for locations of medical items matching the recall information.

28 Claims, 5 Drawing Sheets

RECALL SYSTEM AND METHOD FOR RFID MEDICAL ITEM TRACKING SYSTEM

RELATED APPLICATIONS

This application claims the benefit under 35 USC 119(e) of U.S. Provisional Application No. 61/086,998, filed on Aug. 7, 2008, which is incorporated herein by reference in its entirety.

BACKGROUND OF THE INVENTION

Radio Frequency Identification (RFID) systems have been proposed for the tracking of medical item supplies in hospitals and the entire medical item supply chain. Such systems typically involve one or more readers and many RFID tags, each of which is associated with, such as attached to, items being monitored or tracked. In the case of pharmaceuticals, single-use medical devices, and implantable medical devices, RFID tags are typically affixed to or made part of the pharmaceutical container, e.g., medicine bottle, or medical device container, e.g., disposable packaging for the stent or orthopedic implant. In other cases, the RFID is made part of the medical item itself to allow tracking after consumption or implantation. An advantage of RFID tags is that they are stand-off readable, i.e., readable at a distance without a requirement for contact or a direct line of sight path between the reader and the tag.

RFID tags take the form of integrated circuits, with associated antennas, that encode unique serial numbers. The reader can be in a fixed location or mobile with an operator, and items with RFID tags are detected when they enter or leave the electromagnetic field of the reader. For example, RFID readers are often placed at multiple, distributed locations within a supply chain in order to monitor the items as they pass through manufacturing, transportation, distribution, storage, to consumption. Each reader captures the RFID tag serial numbers of each item as it enters the reader's interrogation field, and data collected from all readers facilitates item tracking over time, through and within the chain and within medical and storage facilities.

Another aspect of medical item management within the supply chain is handling of medical recalls. It is periodically necessary to purge supply chains of medical items that have been recalled. The recall initiators are typically governmental agencies such as the Federal Drug Administration (FDA) but also include the manufacturers of the medical items.

Systems have been proposed that prevent the dispensing of recalled medication. Examples include systems that the automatically deliver unit dose packages or medical fluids to patients. They include a recall function in which recalled products are identified to control servers, which then identify individual medication carriers that contain the recalled medication. The recalled doses of the carriers are then flagged to avoid their being dispensed to patients. In other systems, RFID tags are used to track items allowing a check to be performed before administration against recall data. Others have recognized that, when RFID tags are used to track medical items, the time required to locate products involved in a recall can be reduced.

SUMMARY OF THE INVENTION

In general, according to one aspect, the invention features a medical item recall system for medical items at one or more medical facilities at which the medical items are consumed and/or distributed to patients. Each of the medical items has stand-off readable tags, such as RFID tags. The system comprises medical facilities storage devices at the one or more medical facilities containing medical items, the medical items being identified via the stand-off readable tags and associated with individual medical facilities storage devices. The storage devices typically include storage cabinets that hold the medical items in a storage room. The system further comprises an inventory management system that receives recall information for the medical items, receives content information concerning the medical items contained in each of the medical facilities storage devices, and issues reports for locations of medical items matching the recall information.

In this way, very fine granularity location information is generated for the recalled items, allowing the items to be immediately withdrawn from active inventory.

In the preferred embodiment, the medical item recall system tracks medical items in a supply chain extending between one or more manufacturers of the medical items and the one or more medical facilities at which the medical items are consumed. In this way, recalled medical items are purged from the supply chain.

Preferably, the medical facilities storage devices automatically determine the presence of medical items contained in the medical facilities storage devices by periodically automatically interrogating the stand-off readable tags associated with each one of the medical items.

In further aspects of the preferred embodiment, tracking extends to sales representative storage for each of multiple sales representatives and/or manufacturer storage. Sales representative/manufacturer/distributor scanning devices are provided for scanning the stand-off readable tags of the medical items contained in the storage, the scanning devices reporting content information to the inventory management system. The inventory management system then further issues reports for locations of medical items matching the recall information including the storage locations.

Typically, the recall information includes a recall class indicating a priority of the recall, a recall date, and product identification information.

Different reports are preferably available. Manufacturer reports characterize the inventory of the medical items at each of the one or more medical facilities and inventory held by sales representatives in sales representative storage matching the recall information. Hospital reports characterize the inventory of the medical items at one or more medical facilities matching the recall information and/or time of use of the medical items matching the recall information.

Other features are preferably included such as upon associating the medical items with the stand-off readable tags, the system confirms whether the medical items match the recall information. The system also confirms whether the medical items match the recall information prior to use at the medical facilities, and confirms whether the medical items match the recall information prior to shipment to the one or more medical facilities.

In general, according to another aspect, the invention features a medical item recall monitoring method for medical items at one or more medical facilities at which the medical items are consumed and/or distributed to patients. The method comprises associating each of the medical items with stand-off readable tags, storing the medical items in medical facilities storage devices at the one or more medical facilities, receiving recall information for the medical items, receiving content information concerning the medical items contained in each of the medical facilities storage devices, and issuing reports for locations of medical items matching the recall information.

In general, according to still another aspect, the invention features a medical item recall system for medical items in a supply chain extending from manufacturers to one or more medical facilities at which the medical items are consumed and/or distributed to patients. Each of the medical items has stand-off readable tags. The system comprises medical facilities storage at the one or more medical facilities containing medical items, the medical items being identified via the stand-off readable tags and associated with individual medical facilities storage devices. Sales representative storage for each of multiple sales representatives is used to hold medical items in transit between manufacturers of the medical items, one or more distributors, and/or the medical facilities and sales representative scanning devices are provided for each of multiple sales representatives for scanning the stand-off readable tags of the medical items contained in the sales representative storage, the sales representative scanning devices reporting content information to the inventory management system. Further provided are manufacturer storage for each of the manufacturers of the medical items and distributor storage in the supply chain. An inventory management system receives recall information for the medical items, receives location information concerning the medical items contained in each of the medical facilities storage, sales representative storage, manufacturer storage, and distributor storage, and issues reports for locations of medical items matching the recall information.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
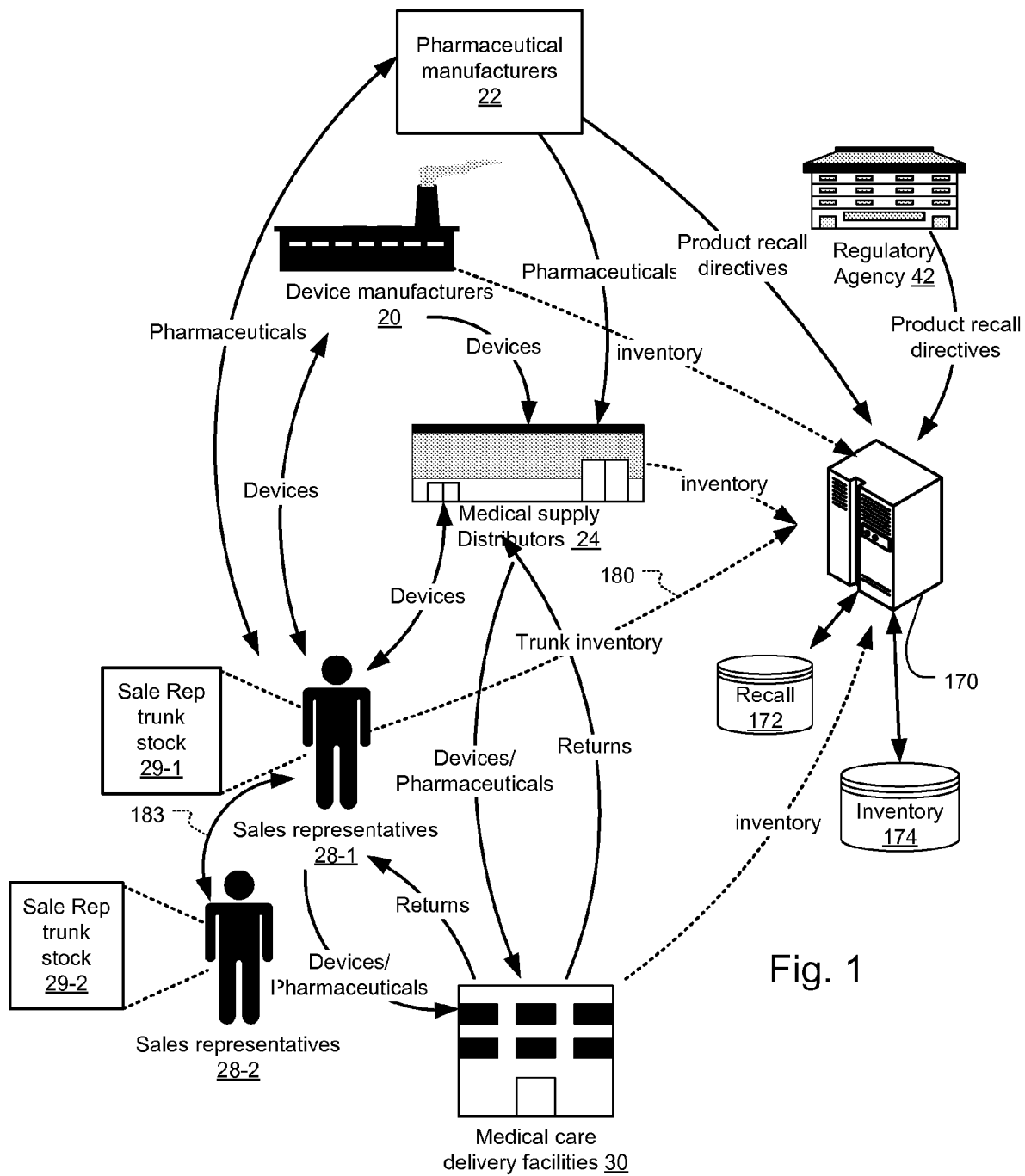
FIG. 1 is a schematic diagram illustrating a medical item supply chain with an inventory tracking system for recalled item tracking according to the present invention.

FIG. 1 illustrates typical aspects of a supply chain for medical devices and pharmaceuticals including the medical device manufacturers 20, pharmaceutical manufacturers 22, medical supply distributors 24, sales representatives 28-1, 28-2, and medical care delivery facilities 30.

The medical devices, a subclass of medical items, include a broad range of devices including classes of devices such as implanted devices (e.g., cardiac stents and joint replacements), disposables (e.g., catheters and hypodermic syringes), and equipment (e.g., imaging and monitoring devices), for example. These medical devices are manufactured by the device manufacturers 20.

Similarly, pharmaceuticals, another subclass of medical items, are manufactured by the pharmaceutical manufacturers 22, e.g., drug companies.

The medical items, e.g., medical devices and pharmaceuticals reach the point of consumption or sale at the medical care delivery facilities 30, which is a broad category including hospitals, doctors' offices, long-term care facilities, correctional facilities, and drugstores/medical supply companies.

In the chain, between the medical device manufacturers 20 and pharmaceutical manufacturers 22, on one hand, and the medical delivery facilities 30, on the other, are often one or more tiers of medical supply distributors 24 and sales representatives 28-1, 28-2, with the sales representatives 28-1, 28-2 representing the distributors 24 and/or manufacturers 20, 22. As is common, these sales representatives 28-1, 28-2 also carry their own inventory or stock of medical items 29-1, 29-2, sometimes termed trunk stock. This trunk stock typically represents items in transit to and from the medical care delivery facilities 30.

In the illustrated example, each of the medical care delivery facilities 30, representatives 28, distributors 24, and/or manufacturers 20, 22 provide inventory, shipping and usage information to an inventory management system 170. Thus, in this example, inventory management system 170 tracks the movement of medical items, including medical devices and pharmaceuticals, through the entire supply chain. It maintains this information in an inventory database 174.

In other examples, the inventory management system 170 covers only a portion of the supply chain or even a single layer of the supply chain (medical care delivery facilities 30 or representatives 28 or distributors 24) or a business entity within the chain, such as at the medical care delivery facilities 30 or groups of commonly managed facilities. In still other examples, the inventory management system 170 tracks medical items between the medical care delivery facilities 30, sales representatives 28, and manufacturers 20, 22 for individual manufacturers.

In the preferred embodiment, the inventory management system 170 is a state-based system that utilizes radio frequency identification (RFID) tags to determine the medical items held in inventory, transferred within the supply chain, and/or consumed at facilities 30. Aspects of the system are also described in U.S. Pat. No. 7,639,136, entitled RFID Medical Supplies Consumption Monitoring System and Method, by Wass et al., which is incorporated herein in its entirety by this reference.

According to an aspect of the invention, the inventory management system 170 further receives recall directives. Typically the recalls are initiated by a governmental agency 42, such as the FDA, or by the manufacturers 20, 22 of the medical items. The recall directives identify medical items that are deemed unsafe or should otherwise no longer be used. In some cases the directives identify entire product families. In other examples, the medical items are identified by a stock keeping unit (SKU) identifier. In still other examples, in which only a production lot of medical items is being recalled, the medical items subject to recall are identified by a combination of a SKU and a lot number or serial number.

In some examples, the recall directives are manually entered into the inventory management system 170 by operators tasked with monitoring for such recalls. In other examples, the inventory management system 170 automatically enters the recall directives in response to messages from the recall initiator and/or the inventory management system 170 periodically automatically retrieves the recall information from websites on which such information is disseminated by the recall initiator.

In one example, the recall directives flow to the inventory management system 170 in automated or email based processes from the manufacturers or the FDA. For example, the FDA Class I recalls are currently distributed in email notifications. Class II and III recalls are currently searchable.

A recall database 172 is the data structure maintained by the inventory management system 170 that holds product recalls at the model, serial number and lot number level.

In other examples, the recall directives are provided in data feeds established by the FDA or medical device manufacturers to distribute recall information more rapidly and more reliably without the need for human intervention. These data are automatically populated into the recall database 172. In some cases, the automated feeds are obtained from a third party aggregator, where this third party collects it from the FDA 42 and manufacturers 20, 22 and provides it as a single source feed to the inventory system 170.

Figure 2:
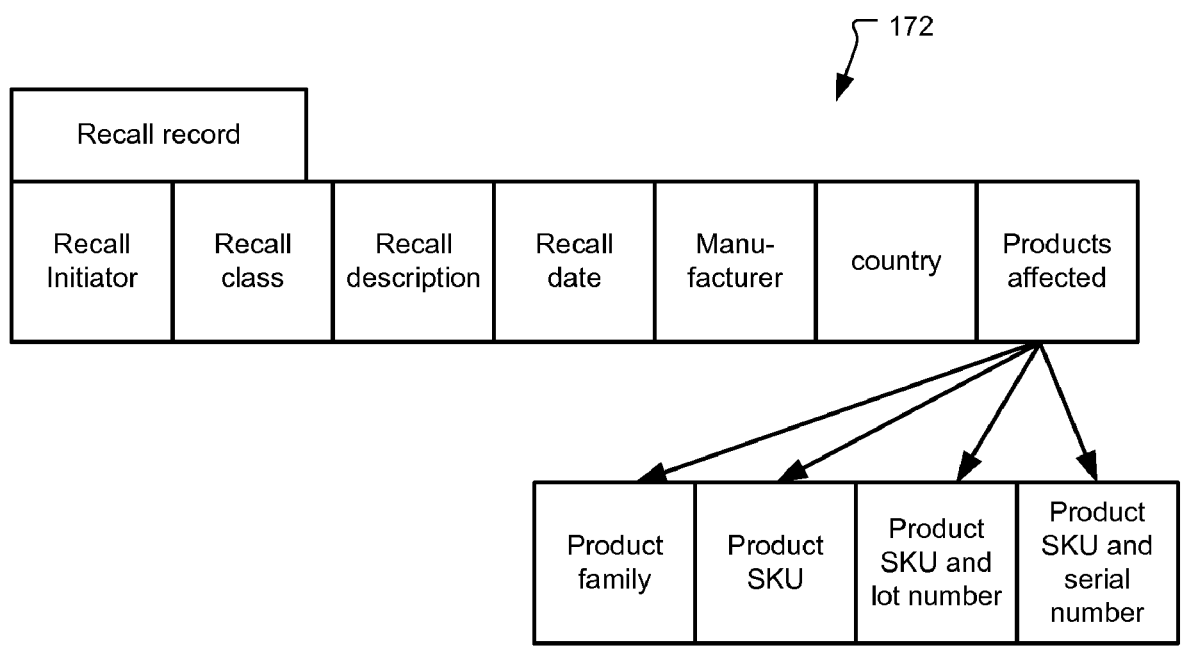
FIG. 2 illustrates database structure for storing recall information.

FIG. 2 shows the information contained in records of the recall database 172 maintained by the inventory management system 170. The idea is to be able to hold product recall information in recall records, and cross reference that with item-level data in order to generate the appropriate set of alerts, informational messages, and data feeds.

In more detail, each record in the recall database 172 maintained by the inventory management system 170 comprises the following fields:

recall initiator: the FDA 42 or a manufacturer 20, 22;
recall class (i.e. urgency and priority, e.g., class I, II, III);
recall description: text field for additional information;
recall date, the date the recall was initiated by FDA, for example;
manufacturer: company name of manufacturer of recalled medical item;
country: country of origin of item;
The medical items affected, are identifiable at one of the following levels within each record:
product family,
product SKU,
product SKU and lot number, or
product SKU and serial number.

Figure 3:
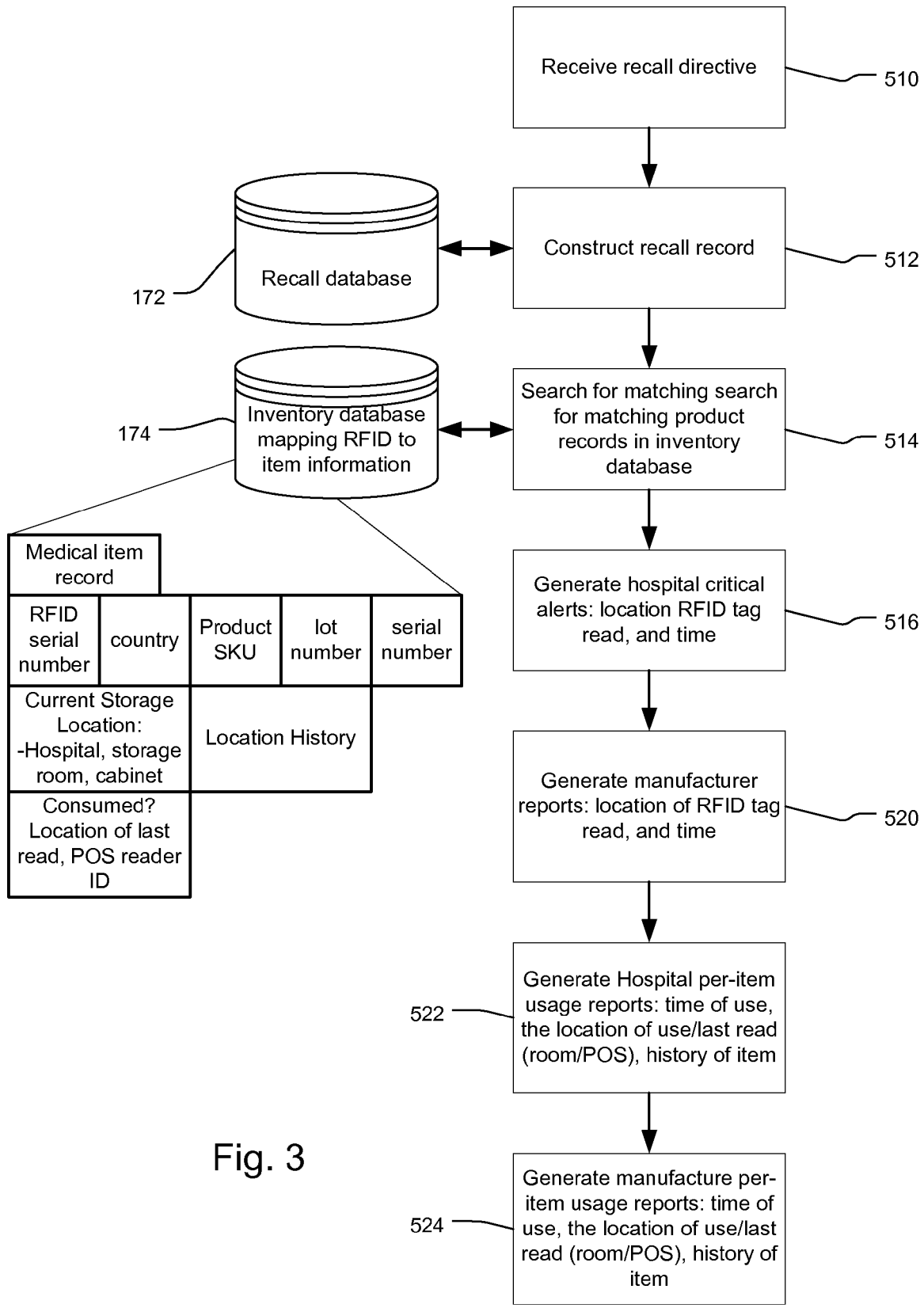
FIG. 3 is a flow diagram illustrating the method for finding and reporting medical items subject to a recall directive according to the present invention.

FIG. 3 shows the method by which the medical items in the supply chain are monitored, identified, and located for recall.

In step 510 the recall directives are received into the inventory management system 170, which then constructs the recall record and stores that record into the recall database 172 in step 512.

In step 514, the inventory management system 170 searches for products in the supply chain that match the recall record. This is performed by accessing the inventory database 174, which contains records for each medical item in the supply chain. In more detail, the inventory database 174 is indexed by the RFID serial number associated with each medical item. The medical item records also store the SKU, lot number and serial number for each item, in addition to its location within the supply chain. The inventory management system 170 searches for medical items that match the conditions of the recall.

When items matching the recall are found, the associated location of the medical items is returned from the database 174. This includes fine granularity location information, including not only the particular manufacturer 20, 22, distributor 24 or medical care delivery facility 30, but the storage room 110, and particular cabinet 150, 150-$s$, or trunk stock location 29 containing the recalled medical item (see FIG. 4).

In the preferred embodiment, additional information is preferably returned by the database 174 including whether the medical item has been consumed, e.g., used or implanted. The location of the last RFID read is returned when the item was no longer being tracked by the inventory management system. Here it is assumed that the item was consumed. The location of last read by a point of service RFID reader is returned also when the item is no longer being tracked. This is interpreted as the known consumption of the item.

In step 516, the inventory management system 170 generates a hospital critical alert. This report is typically generated for each medical care delivery facility 30. It indicates whether each facility 30, such as hospital, has inventory that matches the recall. The report includes the location, storage room and cabinet of the recalled medical items. If the medical items are no longer detectable by the system, the report includes the location and RFID reader where the RFID tags of these medical items where last read, and the time of this read.

In step 520, the inventory management system 170 generates a manufacturer report, if required. Manufacturer reports include a list of the recalled items and the distribution center 24 and storage depot inventory within the manufacturers 20, 22 where the recalled items are stored. The report also includes the recalled items held in trunk stock 29 by sales representatives and the particular storages devices 150 at medical care facilities 30 that contain recalled items. Generally, the report includes the location of each medical item matching the recall including product information and quantity, and preferably further includes storage room 105, 110 and storage cabinet 150 in which the recalled medical items reside, throughout the entire medical item supply chain.

All the reports and alerts are typically obtained from a web report, or are pushed to users via data feeds, emails, mobile device reports, for example.

In step 522, the system generates hospital usage reports of used medical items that match the recall criteria. This report is generated for each medical care delivery facility 30 and includes the time of use and the location of use, e.g., room or other point of service (POS), where the RFID tag of the recalled medical item was last read. The entire history of the product item is further displayed, in some examples.

In step 524, the system generates manufacturer usage reports of used or assumed used medical items for all recalled medical items produced by the manufacturer 20, 22. Typically medical items are assumed to be used by the system when the associated RFID tag is no longer being read by any RFID readers in the supply chain and/or was read by a point of service (POS) RFID reader. The report includes the location of use (Hospital/room/POS) and time of use. If the item is assumed used, then the system displays the location and time of the last read by an RFID reader/device.

Figure 4:
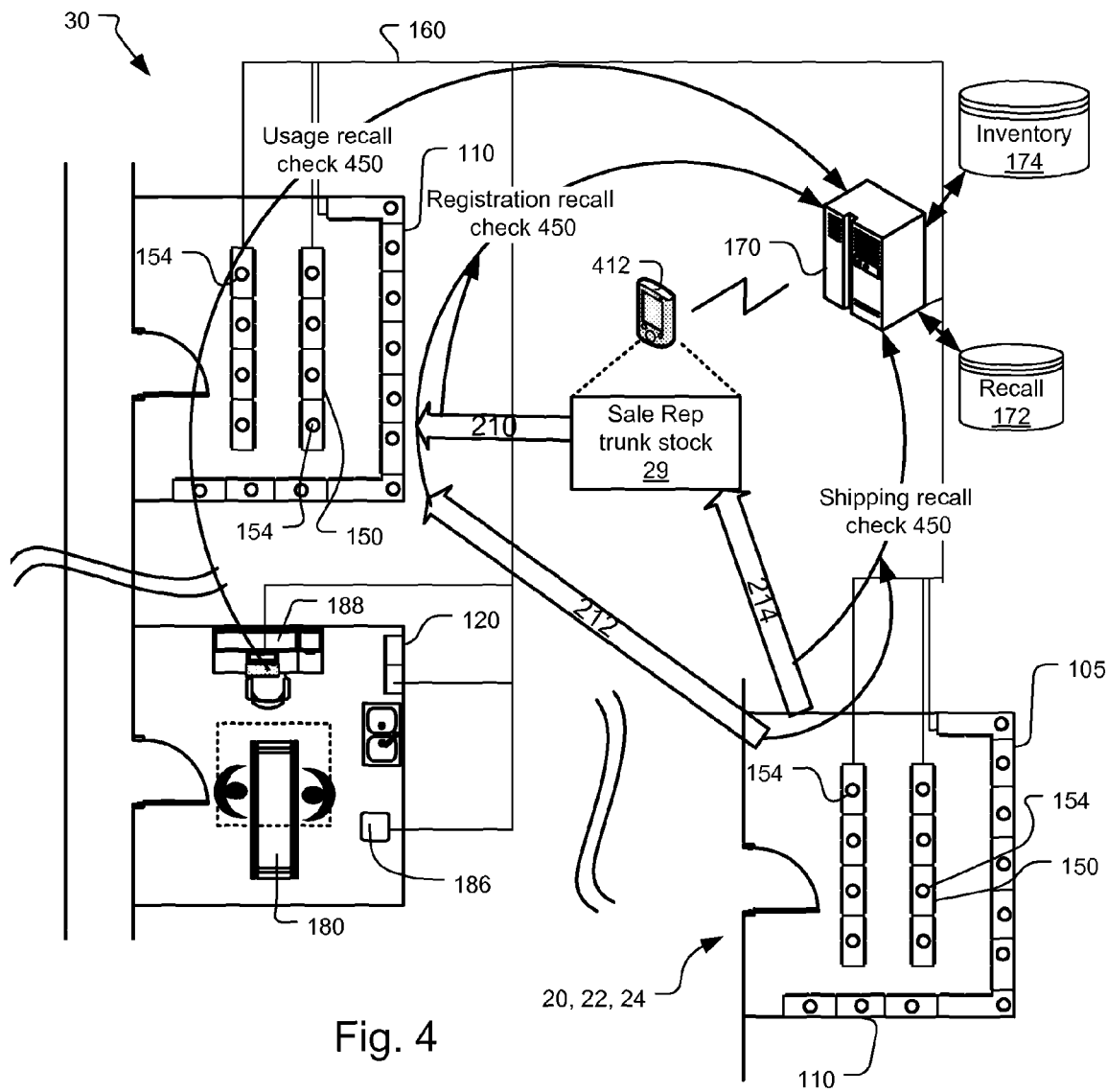
FIG. 4 is a schematic diagram illustrating a medical item tracking system with tacking and usage reporting according to the present invention.

FIG. 4 illustrates how the medical items are tracked within and between medical care delivery facilities 30, sales representatives' trunk stock 29-1, 29-2, distributors 24, and manufacturers 20, 22.

The hospital or other medical care facility 30 generally comprises a medical supply room 110, which is devoted to housing supplies including medical items, and a procedure room 120 where the medical items are consumed, such as used or implanted in patients.

In more detail, the medical supply room 110 in the example comprises a number of medical supply cabinets or other storage devices 150. In the preferred embodiment, each of the medical supply cabinets 150 is a radio frequency identification (RFID) cabinet that includes an associated RFID reader 154. These medical supply room/cabinet readers 154 are capable of detecting and reading RFID tags of medical items stored in the cabinets 150.

The RFID cabinet readers 154 of the medical supply location 110 are networked onto a communications network 160. Specifically, the cabinet readers 154 communicate via the communications network 160 to the inventory management system 170. In this way, the inventory management system 170 is able to track the presence of the medical items in the storage cabinets 150 in real-time without intervention by staff. Thus, no action is required by the hospital personnel in order to enable the inventory management system 170 to detect the presence of the medical items. Further, there is no staff intervention required when items are removed since the periodic scans of the cabinet contents by the readers 154 detect removal, which is then reported to the inventory management system 170. Finally, this inventory tracking system, being RFID-based, is able to track each item in inventory, uniquely, according to the unique serial number encoded in each RFID tag.

In other examples, the medical supply room 110 has standard medical supply cabinets or other storage units, which do not have integrated RFID readers. In this example, the inventory of the room must be maintained manually through the use of staff-operated mobile readers.

Most often the medical items are removed from the medical supply location 110 when they are going to be used in the treatment of patients at the facility in a procedure room, or other POS. In some examples, these procedure rooms 120 are simply patient examining rooms for simple procedures such as injections. In other examples, the procedure room 120 is an operating room, a diagnostic or monitoring room, or a dedicated-use room such as a catheterization laboratory (cathlab), or control room for a cathlab. In other examples, the procedures are performed in interventional radiology rooms, electro-physiology rooms and/or rooms for orthopedics.

The procedure room 120 has one or more associated procedure room POS RFID readers, in some implementations. In the illustrated example, the procedure room has an RFID POS reader associated with a refuse container 186 system and/or an RFID POS reader associated with a workstation 188. These RFID readers are used to detect the usage of the medical items in the context of the procedure being performed by medical professionals, on a patient on table 180. When a RFID tag of a medical item is scanned by a procedure room RFID POS reader or other reader at a POS, the medical item is assumed to have been used or consumed.

When the RFID tag of a recalled item is read by the RFID reader of the POS, see readers 186, 188, the inventory management system 170 confirms that the item is not subject to recall, see arrow 450. If it is, a warning (audible and visual) is sent to the user as an indicator that this item should not be used. These events are also logged for auditing at a future time.

As also illustrated, medical items are stored in supply rooms or depots 105 at the distributors 24 and manufacturers 20, 22. In the illustrated example, the items here are tracked automatically using networked medical supply cabinet or other storage devices 150 having medical supply room/cabinet readers 154, which are capable of detecting and reading RFID tags of medical items stored in the cabinets 150. This information is similarly reported to the inventory management system 170. In other examples, the inventory information is obtained manually using handheld/mobile RFID readers that associate the medical items with specific storage devices 150 since there is typically better control over access to the supply rooms at the distributors 24 and manufacturers 20, 22 thus lower the need for automatic RFID tag scanning.

The inventory carried by the sales representatives in the trunk stock 29 is also shown. The representative typically uses a mobile inventory client system 412 to collect inventory information, which the client system 412 sends to the inventory management system 170.

Generally, the mobile inventory client system 412 is a handheld device possibly built on personal digital assistant (PDA) platform. As such, it is battery powered. In a preferred embodiment, it has both cellular data and WIFI data transmission capabilities, enabling it to access the inventory system 170.

Also shown are the paths by which medical items move between the storage locations. Arrow 210 illustrates movement of medical items back and forth between the sales representative's trunk stock 29 and the medical care delivery facilities 30. Arrows 212 and 214 illustrate movement of medical items between the distributors 24 and manufacturers 20, 22 and to and from the medical care delivery facilities 30 and the trunk stock 29.

The mobile reader 412 of the sales representative is used to record transactions of medical items between the trunk stock 29 and the medical care delivery facilities 30 (210) and between trunk stock 29 and distributors 24 and manufacturers 20, 22 (214). In further examples, the mobile reader 412 is used to collect an inventory of the supply room 110 especially when standard storage are used, i.e., ones without RFID readers.

In the preferred embodiment, registration checks for the existence of a recall are performed. Here, the inventory management system 170 confirms that medical items are not subject to recall during initial registration. A check is performed to make sure that each medical item has not been recalled before it is associated with the RFID tags. In case it is recalled, a warning/error message displayed on the workstation up and the registration will fail. These events will also be logged for auditing at a future time.

Further, in the preferred embodiment, shipping registration checks for the existence of a recall are performed. When shipping a medical item from a distribution center 24 or manufacturer 20, 22, see arrows 212, 214, the RFID shipping system such as a mobile RFID reader 412 reads the RFID tags to mark its associated item as "Shipped". This information is reported to the inventory management system 170, see arrows 450. A check performed by the inventory management system 170 to ensure that the medical item is not subject to recall. If it is, then the inventory management system 170 returns an error to the user RFID shipping system to indicate that this item should not be shipped. These events are logged for auditing at a future time.

Figure 5:
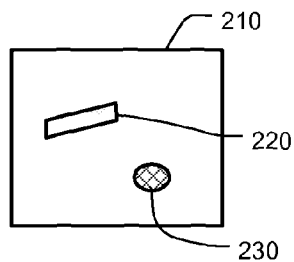
FIG. 5 is a schematic plan view of a medical item with RFID tracking.

FIG. 5 illustrates one way of associating the RFID tags with a medical item. Specifically, a package 210 is provided that contains the medical item 220, typically in a sealed sterile environment. The RFID tag 230 associated with the medical item 220 is attached, fixed or made part of the outside of the packaging 210. In this way, by tracking the RFID tag 230, the medical item package 210, and therefore the medical item 220 is tracked in the hospital or distribution center or manufacturer. In other examples, the RFID tag is incorporated into the medical item itself or adhered to a bottle or package containing the pharmaceutical.

Figure 6A:
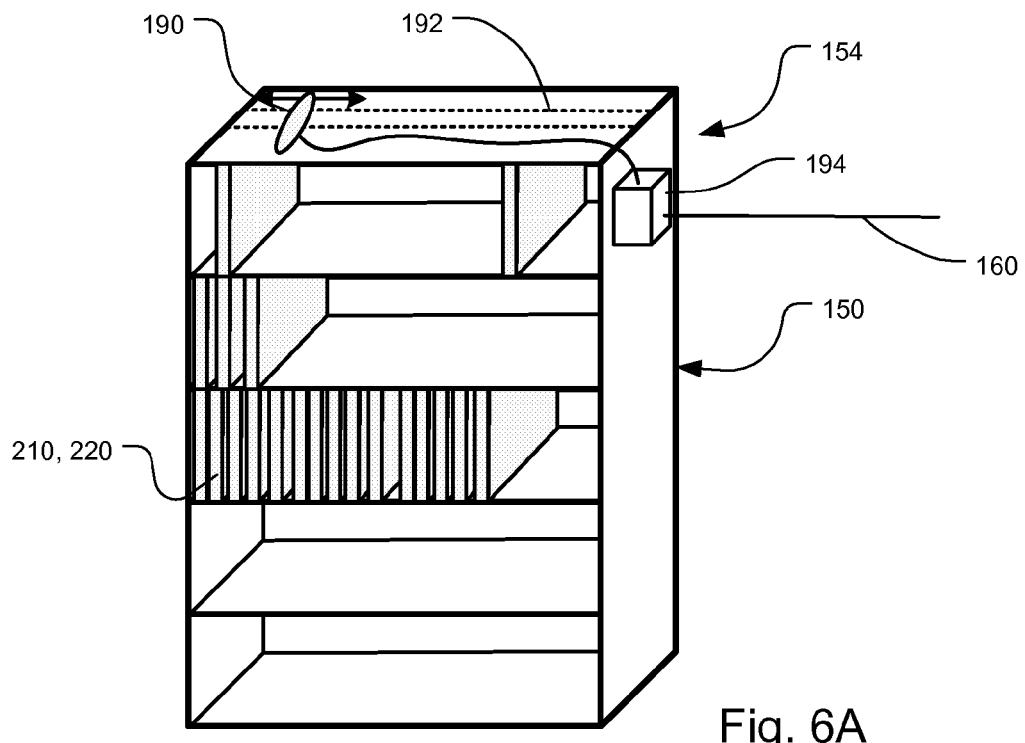
FIG. 6A is a schematic perspective view of an RFID cabinet for storing and automatically scanning and reporting medical items.
Figure 6B:
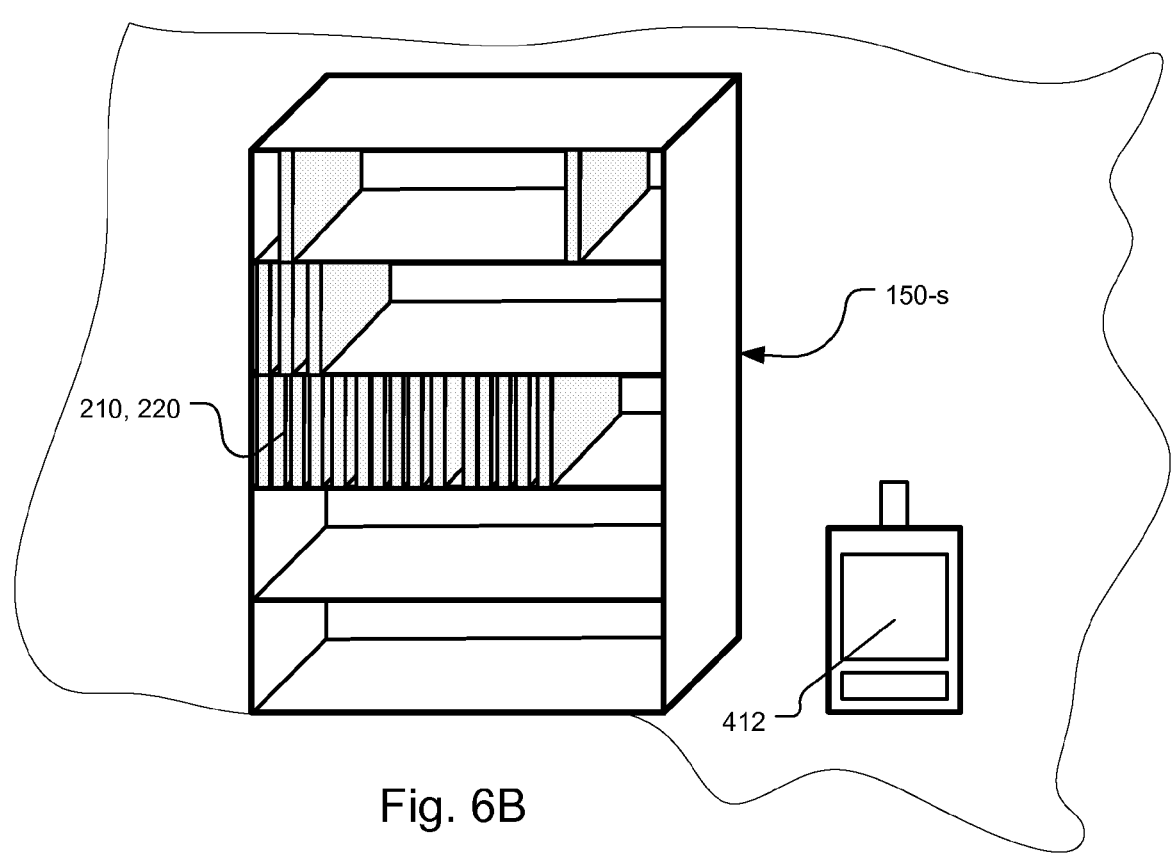
FIG. 6B is a schematic perspective view of a cabinet for storing medical items that are scanned by a mobile reader.

FIGS. 6A and 6B show examples of storage devices, specifically the cabinets 150, 150-s containing medical items 220 stored in item packages 210. In a specific example, they are stored on various shelves. These cabinet-style storage devices are used at medical facilities, in the storage rooms 110, or at distributors/manufacturers 20, 22, 24, in storage rooms or depots 105.

FIG. 6A shows one example of an RFID cabinet 150. The RFID readers 154 for the medical cabinets 150 comprise antennas 190 associated with the cabinets 150 that are periodically moved to enable the RFID readers to scan for RFID tags on medical item packages 210 in the storage cabinets 150. In other examples, stationary antennas are used. This antenna scanning facilitates detection of the tags regardless of orientation within the cabinets or proximity to other RFID tags. In other examples, stationary antennas are used, when scanning is not required.

The RFID controller 194 for the cabinet 150 uses the information transferred from the antenna 190 via wiring 192 to read the RFID tags of the items contained in the cabinet 150. The information is transmitted via a network interface on the controller 194 to the inventory management system 170.

FIG. 6B shows an example of a standard 150-s, which does not have an RFID readers. Instead, the RFID tags on the medical item packages 210 are scanned with a mobile reader 412 which then reports back to the inventory management system 170.

While this invention has been particularly shown and described with references to preferred embodiments thereof, it will be understood by those skilled in the art that various changes in form and details may be made therein without departing from the scope of the invention encompassed by the appended claims.

What is claimed is:

1. A medical item recall system for medical items at one or more medical facilities at which the medical items are consumed and/or distributed to patients, each of the medical items having stand-off readable tags, the system comprising:
   medical facilities storage devices at the one or more medical facilities containing medical items, the medical items being identified via the stand-off readable tags and associated with individual medical facilities storage devices, wherein the stand-off readable tags encode unique serial numbers that uniquely identify corresponding medical items, the medical facilities storage devices reading the stand-off readable tags and reporting the serial numbers read from the stand-off readable tags; and
   an inventory management system tracking each of the medical items according to the serial numbers of the stand-off readable tags, wherein the inventory management system receives recall information for the medical items, receives content information concerning the medical items contained in each of the medical facilities storage devices by receiving the serial numbers read by the medical facilities storage devices, searches an inventory database based on the recall information to determine locations of the medical items based on the reporting of the serial numbers from the stand-off readable tags by the medical facilities storage devices, and issues reports for locations in the medical facilities storage devices of medical items matching the recall information.

2. A medical item recall system as claimed in claim 1, wherein the medical item recall system tracks medical items in a supply chain extending between one or more manufacturers of the medical items and the one or more medical facilities at which the medical items are consumed.

3. A medical item recall system as claimed in claim 1, wherein the medical facilities storage devices automatically determine the presence of medical items contained in the medical facilities storage devices by periodically automatically interrogating the stand-off readable tags associated with each one of the medical items.

4. A medical item recall system as claimed in claim 1, further comprising:
   sales representative storage for each of multiple sales representatives for holding medical items in transit between manufacturers of the medical items, one or more distributors, and/or the medical facilities; and
   sales representative scanning devices for each of multiple sales representatives for scanning the stand-off readable tags of the medical items contained in the sales representative storage, the sales representative scanning devices reporting content information to the inventory management system;
   wherein the inventory management system further issues reports for locations of medical items matching the recall information including the sales representative storage.

5. A medical item recall system as claimed in claim 4, further comprising:
   manufacturer storage for each of the manufacturers of the medical items;
   wherein the inventory management system further issues reports for locations of medical items matching the recall information including the manufacturer storage.

6. A medical item recall system as claimed in claim 1, further comprising:
   manufacturer storage for manufacturers of the medical items;
   wherein the inventory management system further issues reports for locations of medical items matching the recall information including the manufacturer storage.

7. A medical item recall system as claimed in claim 1, further comprising distributor storage devices in the supply chain, the inventory management system further issuing reports for locations of medical items matching the recall information in the distributor storage devices.

8. A medical item recall system as claimed in claim 1, wherein the stand-off readable tags are radio frequency identification (RFID) tags.

9. A medical item recall system as claimed in claim 1, wherein the inventory management system receives the recall information initially generated by a regulatory agency or medical item manufacturer that issues recalls.

10. A medical item recall system as claimed in claim 1, wherein the recall information includes a recall class indicating a priority of the recall, a recall date, and product identification information.

11. A medical item recall system as claimed in claim 1, wherein the reports of the inventory management system include manufacturer reports that characterize inventory of the medical items at each of the one or more medical facilities and inventory held by sales representatives in sales representative storage and any medical items at distributors matching the recall information and inventory held by the manufacturer itself.

12. A medical item recall system as claimed in claim 1, wherein the reports of the inventory management system include hospital reports that characterize inventory of the medical items at one or more medical facilities matching the recall information.

13. A medical item recall system as claimed in claim 1, further comprising medical facilities point of use readers for reading the stand-off readable tags at the point use in the medical facilities, wherein the reports of the inventory management system characterize inventory at one or more medical facilities and time of use of the medical items matching the recall information.

14. A medical item recall system as claimed in claim 1, wherein the inventory management system upon associating the medical items with the stand-off readable tags confirms whether the medical items match the recall information.

15. A medical item recall system as claimed in claim 1, wherein the inventory management system confirms whether the medical items match the recall information prior to use at the medical facilities.

16. A medical item recall system as claimed in claim 1, wherein the inventory management system confirms whether the medical items match the recall information prior to shipment to the one or more medical facilities from manufacturers, distributors or sales representatives.

17. A medical item recall monitoring method for medical items at one or more medical facilities at which the medical items are consumed and/or distributed to patients, the method comprising:
    associating each of the medical items with stand-off readable tags, wherein the stand-off readable tags encode unique serial numbers that uniquely identify corresponding medical items;
    storing the medical items in medical facilities storage devices at the one or more medical facilities, the medical facilities storage devices reading the stand-off readable tags and reporting the serial numbers read from the stand-off readable tags;
    receiving recall information for the medical items;
    an inventory management system receiving content information including the serial numbers read from the stand-off readable tags concerning the medical items contained in each of the medical facilities storage devices to track each of the medical items uniquely according to the serial numbers of the stand-off readable tags;
    the inventory management system searching an inventory database for medical items matching the recall information and then determining locations of the medical items by reference to the content information that was provided by the medical facilities storage devices based on the reporting of the serial numbers from the stand-off readable tags by the medical facilities storage devices; and
    issuing reports for locations of medical items in the medical facilities storage devices matching the recall information.

18. A medical item recall monitoring method as claimed in claim 17, further comprising tracking medical items in a supply chain extending between one or more manufacturers of the medical items and the one or more medical facilities at which the medical items are consumed.

19. A medical item recall monitoring method as claimed in claim 17, further comprising the medical facilities storage devices automatically determining the medical items contained in the medical facilities storage devices by periodically automatically interrogating the stand-off readable tags associated with each one of the medical items.

20. A medical item recall monitoring method as claimed in claim 17, further comprising:
    holding medical items in sales representative storage during transit between manufacturers of the medical items, one or more distributors, and/or the medical facilities;
    scanning the stand-off readable tags of the medical items contained in the sales representative storage;
    reporting content information for the sales representative storage to the inventory management system; and
    issuing reports for locations of medical items matching the recall information including the sales representative storage.

21. A medical item recall monitoring method as claimed in claim 17, further comprising issuing reports for locations of medical items matching the recall information including manufacturer storage.

22. A medical item recall monitoring method as claimed in claim 17, further comprising receiving the recall information initially generated by a regulatory agency and/or manufacturer that issues recalls.

23. A medical item recall monitoring method as claimed in claim 17, further comprising issuing manufacturer reports that characterize inventory of the medical items at each of the one or more medical facilities and inventory held by sales representatives in sales representative storage matching the recall information and inventory held by the manufacturer itself.

24. A medical item recall monitoring method as claimed in claim 17, further comprising issuing hospital reports that characterize inventory of the medical items at one or more medical facilities matching the recall information.

25. A medical item recall monitoring method as claimed in claim 17, further comprising:
    reading the stand-off readable tags at a point use in the medical facilities; and
    issuing reports that characterize inventory at one or more medical facilities and time of use and place of use of the medical items matching the recall information.

26. A medical item recall monitoring method as claimed in claim 17, further comprising, upon associating the medical items with the stand-off readable tags, confirming whether the medical items match the recall information.

27. A medical item recall monitoring method as claimed in claim 17, further comprising, prior to use of the medical items, confirming whether the medical items match the recall information.

28. A medical item recall monitoring method as claimed in claim 17, further comprising confirming whether the medical items match the recall information prior to shipment to the one or more medical facilities.

* * * * *